US010816521B2

(12) United States Patent
Sohn

(10) Patent No.: US 10,816,521 B2
(45) Date of Patent: Oct. 27, 2020

(54) SENSOR HUB AND METHOD FOR OPERATING THE SAME

(71) Applicant: LG ELECTRONICS INC., Seoul (KR)

(72) Inventor: Sungyong Sohn, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 218 days.

(21) Appl. No.: 15/854,960

(22) Filed: Dec. 27, 2017

(65) Prior Publication Data
US 2018/0188218 A1      Jul. 5, 2018

(30) Foreign Application Priority Data

Jan. 3, 2017   (KR) .................. 10-2017-0000533

(51) Int. Cl.
*G01N 15/06*      (2006.01)
*G01N 33/00*      (2006.01)
(Continued)

(52) U.S. Cl.
CPC .......... *G01N 33/0031* (2013.01); *G01K 1/20* (2013.01); *G01N 15/06* (2013.01);
(Continued)

(58) Field of Classification Search
CPC ................................................ G01N 33/0031
(Continued)

(56) References Cited

U.S. PATENT DOCUMENTS 5,428,964 A * 7/1995 Lobdell .................. G05D 27/02
                                                                 62/176.6
6,929,684 B2   8/2005 Chang et al.
(Continued)

FOREIGN PATENT DOCUMENTS

CN        202661101        1/2013
KR       10-0933634       12/2009
(Continued)

OTHER PUBLICATIONS

PCT International Search Report dated Feb. 13, 2018 issued in Application No. PCT/KR2017/013492.
(Continued)

*Primary Examiner* — Walter L Lindsay, Jr.
*Assistant Examiner* — Philipmarcus T Fadul
(74) *Attorney, Agent, or Firm* — Ked & Assocaites LLP

(57) ABSTRACT

The present disclosure relates a sensor hub that allows users to visually and easily check the air environment and power consumption of a room, and a method for operating the same. The sensor hub may include a housing having ventilation ports on lateral and rear sides. A fine dust sensor may be provided to sense a concentration of fine dust introduced through the ventilation ports. A $CO_2$ sensor may be provided in the housing that senses a concentration of $CO_2$. A display plate and a display unit and an illumination plate including a plurality of light emitting units may be provided in the housing. A main board and processor may be disposed in the housing to control the plurality of light emitting units and the display unit based on data on the fine dust concentration and the $CO_2$ concentration received respectively from the fine dust sensor and the $CO_2$ sensor.

15 Claims, 10 Drawing Sheets

(51) Int. Cl.
    *G01R 13/02*     (2006.01)
    *G01K 1/20*     (2006.01)
    *G01R 21/00*     (2006.01)

(52) U.S. Cl.
    CPC ..... *G01N 33/0063* (2013.01); *G01N 33/0073* (2013.01); *G01R 13/0209* (2013.01); *G01R 21/00* (2013.01)

(58) Field of Classification Search
    USPC .......................................................... 73/28.01
    See application file for complete search history.

(56) References Cited

U.S. PATENT DOCUMENTS

| | | | |
|---|---|---|---|
| 2015/0256665 A1 | 9/2015 | Pera et al. | |
| 2015/0285755 A1* | 10/2015 | Moss | G01N 33/0032 |
| | | | 702/133 |
| 2015/0316589 A1* | 11/2015 | Mazara Diaz | G01R 19/165 |
| | | | 324/114 |
| 2016/0034024 A1* | 2/2016 | Mergen | G06F 1/3296 |
| | | | 713/323 |
| 2016/0098916 A1* | 4/2016 | Bieser | G08B 19/00 |
| | | | 340/539.1 |

FOREIGN PATENT DOCUMENTS

| | | |
|---|---|---|
| KR | 10-2015-0068160 | 6/2015 |
| KR | 10-2016-0000879 | 1/2016 |
| KR | 10-2016-0019577 | 2/2016 |
| KR | 10-2016-0097708 | 8/2016 |

OTHER PUBLICATIONS

European Search Report dated Mar. 7, 2018 issued in Application No. 17210872.2.

* cited by examiner

SENSOR HUB AND METHOD FOR OPERATING THE SAME

CROSS-REFERENCE TO RELATED APPLICATION(S)

This application claims the priority of Korean Patent Application No. 10-2017-0000533 filed on Jan. 3, 2017, in the Korean Intellectual Property Office, the disclosure of which is hereby incorporated by reference in its entirety.

BACKGROUND

1. Field

The present disclosure relates to a sensor hub and a method for operating the same, and more particularly, to a sensor hub that allows users to visually and easily check the air environment and power consumption of a room, and a method for operating the same.

2. Background

Techniques for constructing a network in a certain space such as a home or an office using devices that communicate with each other by wired/wireless are known. Various types of devices having a communication function are connected to the network.

A network has been conventionally established by connecting home appliances such as a washing machine, a refrigerator, an air conditioner and the like to an access point (AP) connected to the Internet by wired/wireless and information has been shared with the home appliances via a terminal (for example, a smart phone) connected to the Internet. However, this system is limited in the functions that can be implemented through the terminal because the information obtained from the home appliance is limited. For example, when controlling the refrigerator through the terminal, since sensors provided in the refrigerator cannot be changed, information that the terminal can share with the refrigerator is also limited.

Recently, an IoT (Internet of Things) technology has been attracting attention as a technology that can overcome these problems. This is a technology that allows information to be shared among things by connecting the things over a wired/wireless network. The IoT technology adds communication and sensor functions, etc. to various devices so that the devices themselves can automatically transmit, receive and process information.

In response to such diversified network environments, a hub is emerging as a device that manages devices integrally and communicates more actively with users based on information shared with the devices.

However, while the conventional hub concentrates on transmitting/receiving information to/from peripheral devices using the IoT technology, it has a problem that the function of providing useful information to users by using built-in sensors is fragile.

Even in case where the hub can provide useful information to the users by using the built-in sensors, there is a problem that the detection efficiency and accuracy of the built-in sensors are degraded due to the appearance and structure focused only on downsizing and weight saving. There is also a problem that it is difficult for the users to visually and easily grasp the information sensed by the sensors.

BRIEF DESCRIPTION OF THE DRAWINGS

Embodiments will be described in detail with reference to the following drawings in which like reference numerals refer to like elements, and wherein.

DETAILED DESCRIPTION

Figure 1:
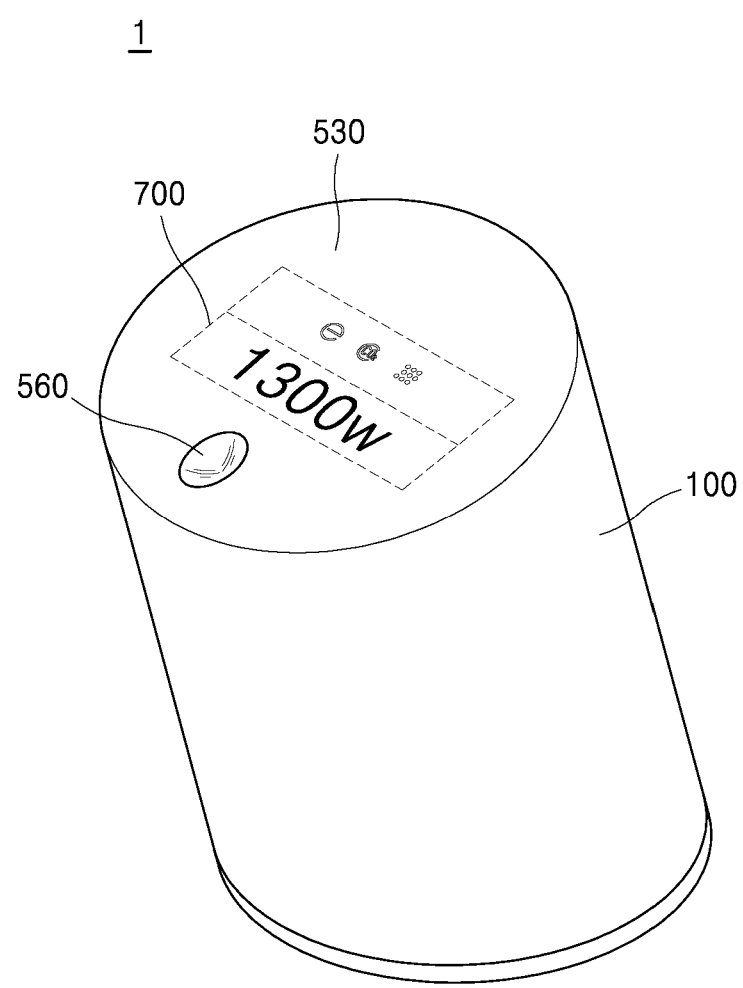
FIG. 1 is a perspective view illustrating a sensor hub according to an embodiment of the present disclosure.

The above objects, features and advantages will become apparent from the detailed description with reference to the accompanying drawings. Embodiments are described in sufficient detail to enable those skilled in the art in the art to easily practice the technical idea of the present disclosure. Detailed descriptions of well-known functions or configurations may be omitted in order not to unnecessarily obscure the gist of the present disclosure. Hereinafter, embodiments of the present disclosure will be described in detail with reference to the accompanying drawings. Throughout the drawings, like reference numerals refer to like elements.

Hereinafter, a sensor hub according to an embodiment of the present disclosure will be described with reference to FIGS. 1 to 9.

Figure 2:
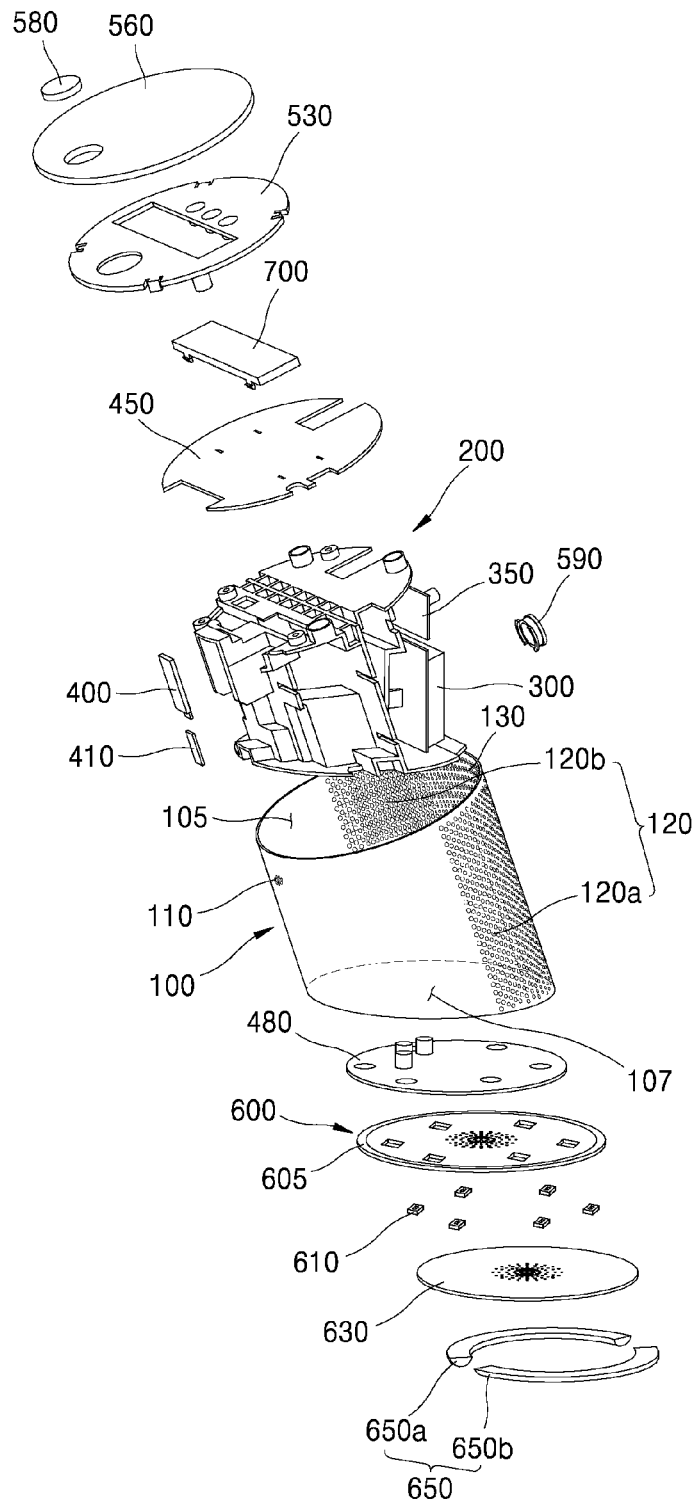
FIG. 2 is an exploded perspective view illustrating the sensor hub of FIG. 1.
Figure 3:
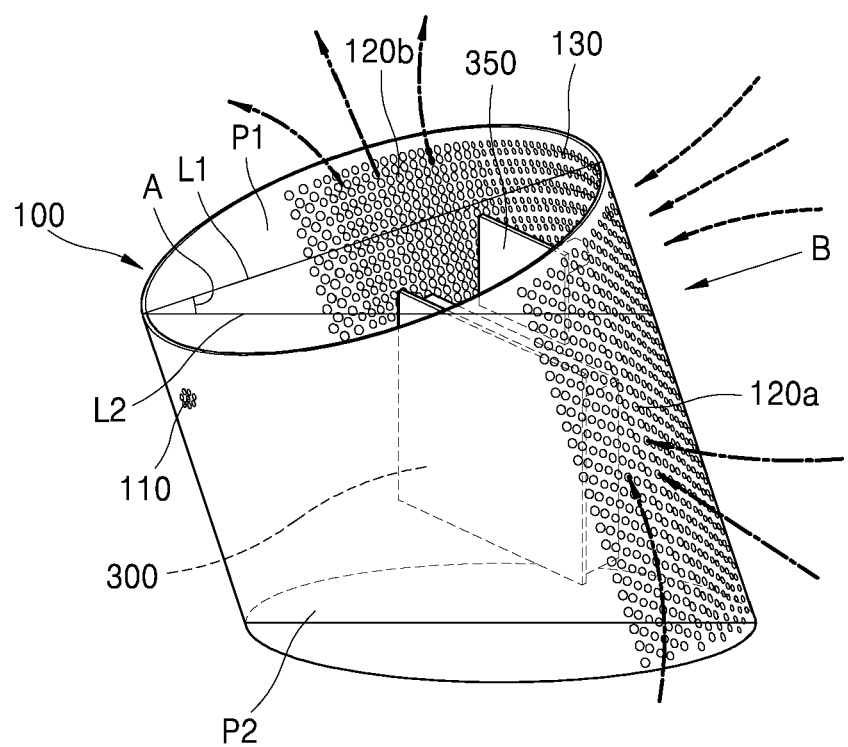
FIGS. 3 and 4 are views illustrating the structure of a housing of the sensor hub of FIG. 1 and a flow of air introduced into the housing.
Figure 4:
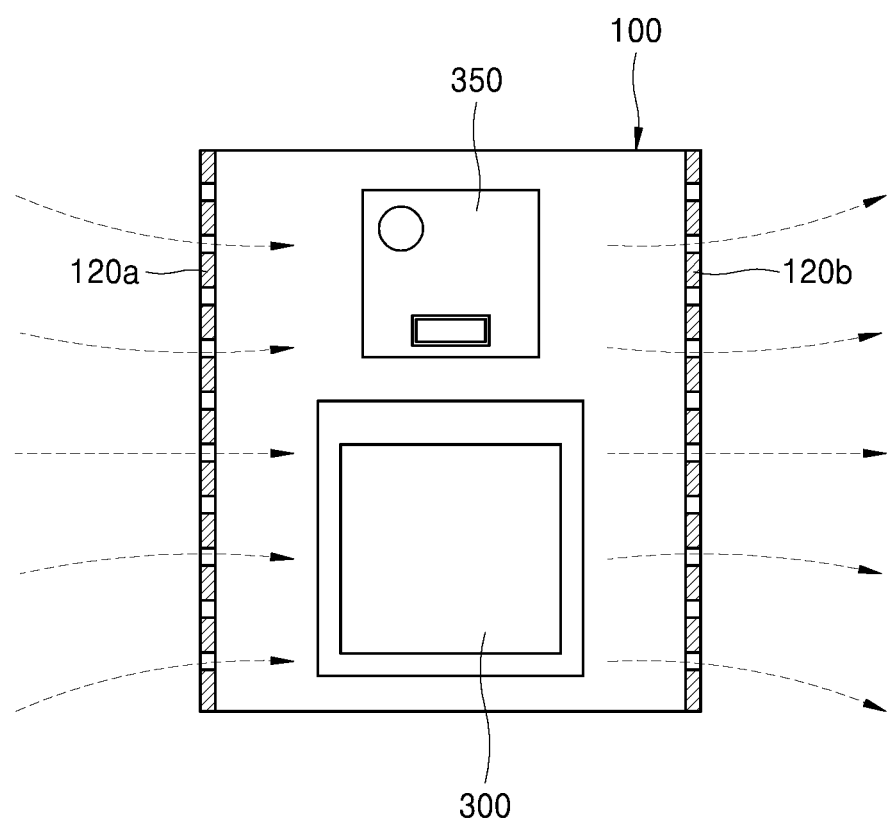
Figure 5:
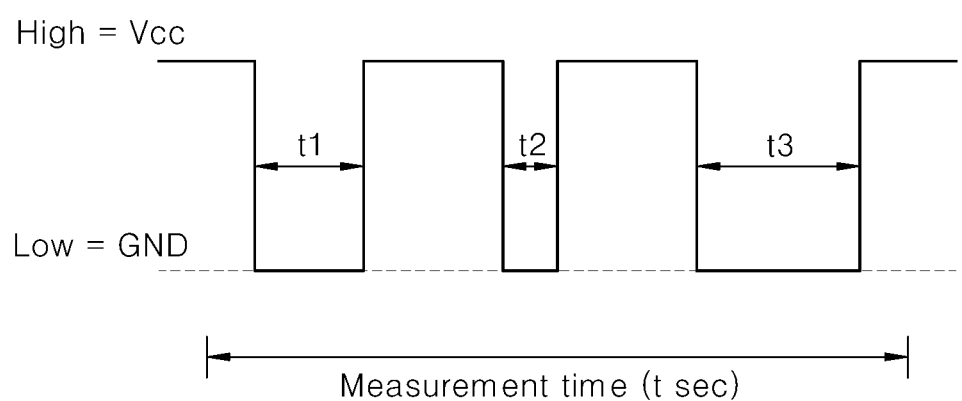
FIG. 5 is a view for explaining the calculation logic of a fine dust sensor incorporated in the sensor hub of FIG. 1.
Figure 6:
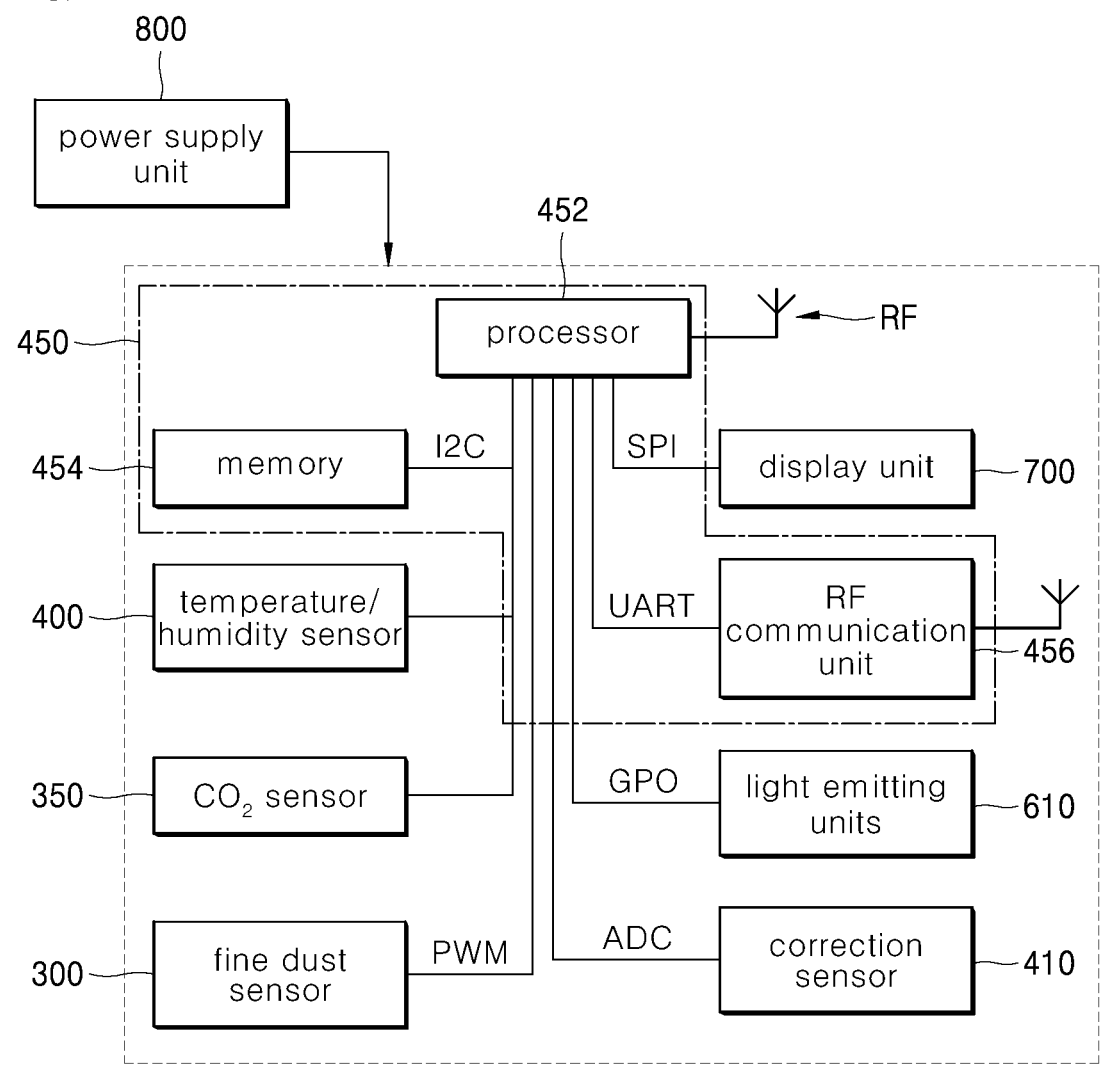
FIG. 6 is a block diagram for explaining a method of communication between components in the sensor hub of FIG. 1.
Figure 7:
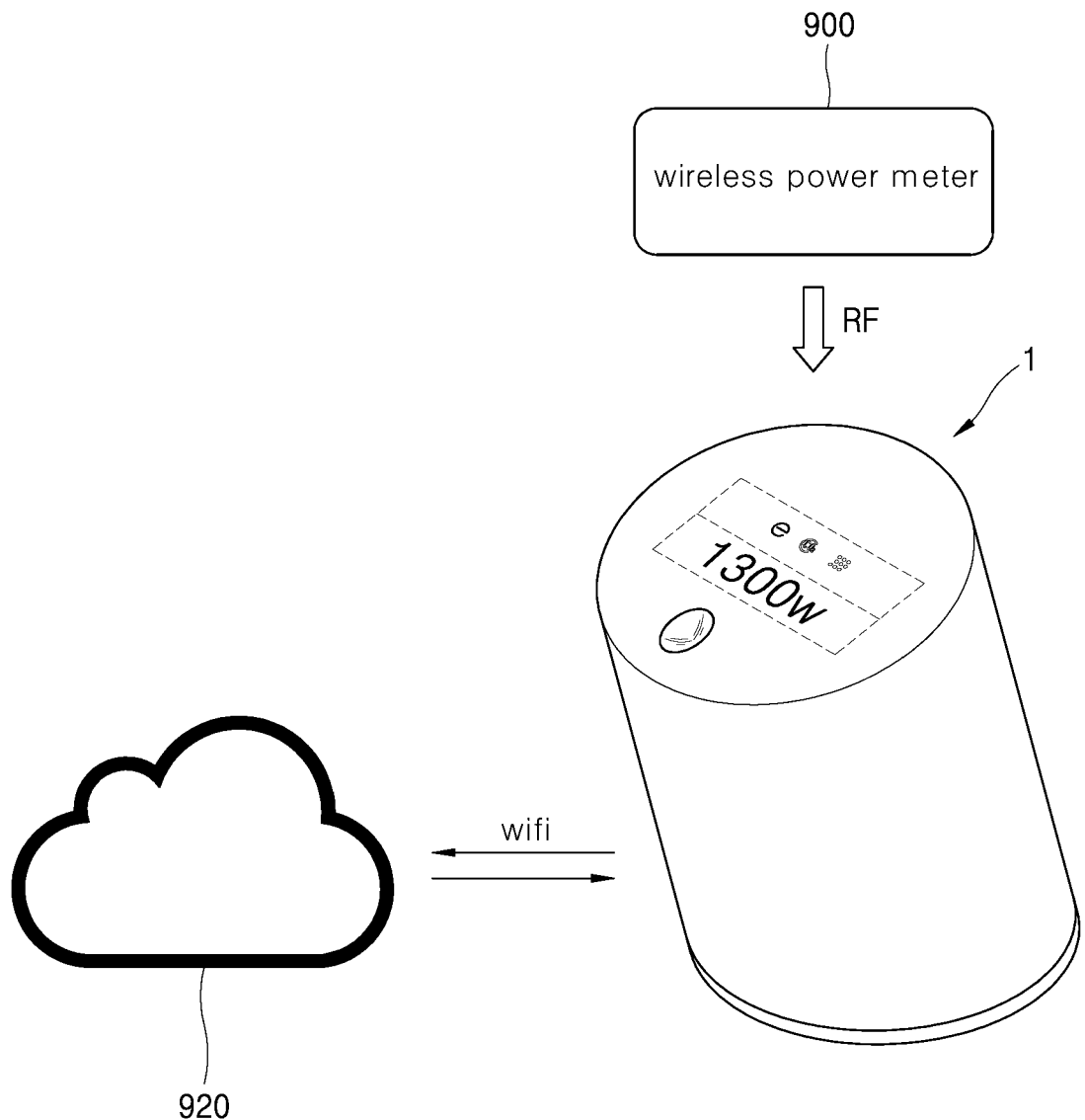
FIG. 7 is a schematic view for explaining how the sensor hub of FIG. 1 communicates with an external server or a device.
Figure 8:
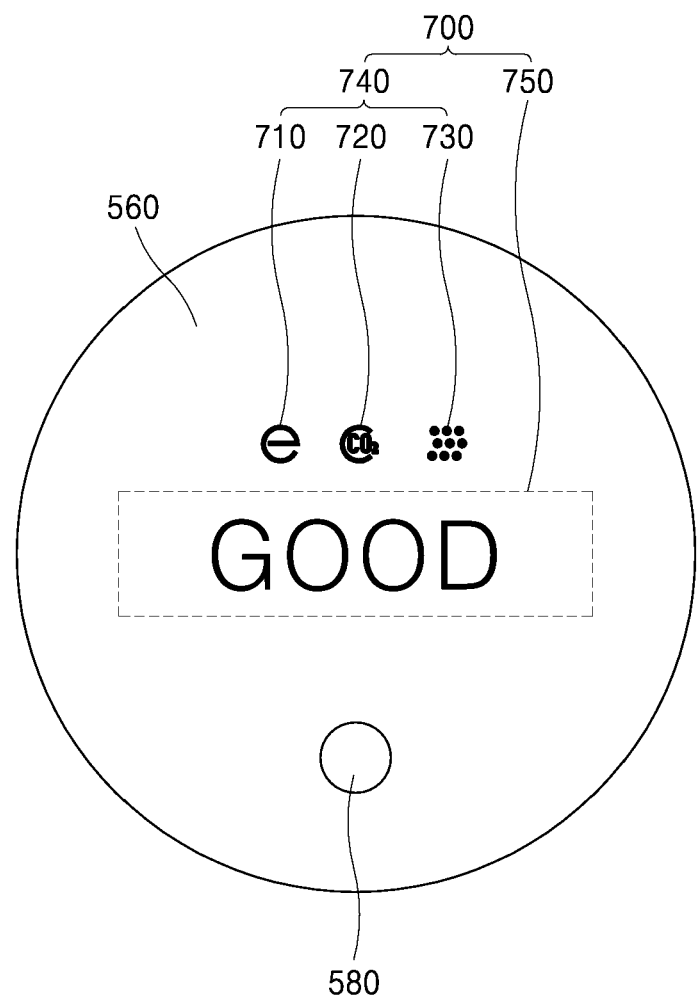
FIGS. 8 and 9 are views illustrating a display unit of the sensor hub of FIG. 1.
Figure 9:
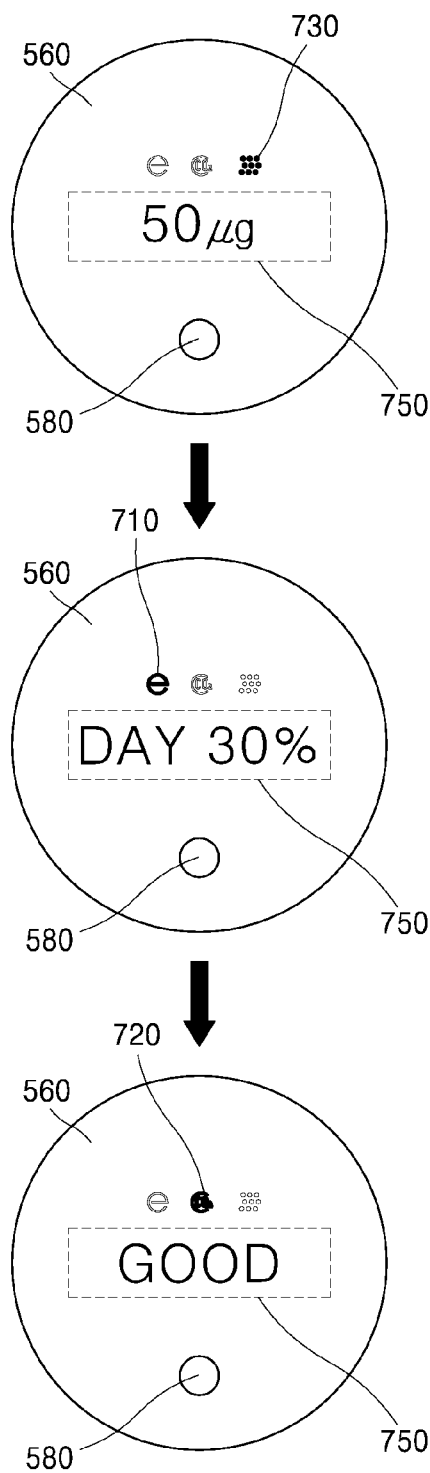

FIG. 1 is a perspective view illustrating a sensor hub according to an embodiment of the present disclosure. FIG. 2 is an exploded perspective view illustrating the sensor hub of FIG. 1. FIGS. 3 and 4 are views illustrating the structure of a housing of the sensor hub of FIG. 1 and a flow of air introduced into the housing. FIG. 5 is a view for explaining the calculation logic of a fine dust sensor incorporated in the sensor hub of FIG. 1. FIG. 6 is a block diagram for explaining a method of communication between components in the sensor hub of FIG. 1. FIG. 7 is a schematic view for explaining how the sensor hub of FIG. 1 communicates with an external server or a device. FIGS. 8 and 9 are views illustrating a display unit of the sensor hub of FIG. 1.

First, referring to FIGS. 1 and 2, a sensor hub 1 according to an embodiment of the present disclosure may include a housing 100, a support bracket 200, a fine dust sensor 300, a $CO_2$ sensor 350, a temperature/humidity sensor 400, a correction sensor 410, a main board 450, a display unit 700, a display plate 530, a top plate 560, a first input unit 580, an illumination control board 480, a second input unit 590, an illumination plate 600, a plurality of light emitting units 610 and a bottom plate 630.

The housing 100 may have ventilation ports 120 and 130 on its lateral and rear sides, respectively, and may have a first opening 105 and a second opening 107 at its top and bottom, respectively.

Specifically, the housing 100 may have a front ventilation port 110 in the front, a first side ventilation port 120a and a second side ventilation port 120b in the side, and a rear ventilation port 130 in the rear.

All of the ventilation ports 110, 120 and 130 recited in the present disclosure each may include a plurality of vents and the shapes and numbers of vents may be the same or different.

The temperature/humidity sensor 400 may be disposed adjacent to the front ventilation port 110 and the $CO_2$ sensor 350 and the fine dust sensor 300 may be disposed adjacent to the rear ventilation port 130.

Here, the $CO_2$ sensor 350 may be disposed at the top of the fine dust sensor 300 and the $CO_2$ sensor 350 and the fine dust sensor 300 may be interposed between the first side ventilation port 120a and the second side ventilation port 120b.

Such a structure of the housing 100 (i.e., the positions of the first side ventilation port 120a and the second side ventilation port 120b) enables the fine dust sensor 300 to easily detect fine dusts.

Specifically, referring to FIGS. 3 and 4, air introduced through the first side ventilation port 120a is discharged through the second side ventilation port 120b, and the fine dust sensor 300 is disposed in a path through which the air introduced through the first side ventilation port 120a passes. For example, the first side ventilation port 120a may be provided on an opposite side of the housing 100 relative to the second side ventilation port to promote air flow through the housing 100. Moreover, the fine dust sensor 300 may be positioned relative to the ventilation ports 120 so that airflow is not obstructed. For example, the fine dust sensor 300 may have a shape that is elongated having a wide side and a narrow side, and hence, the fine dust sensor 300 may be oriented such that it extends from the first side to the second side lengthwise. Since the wide side of the sensor is positioned to face the rear ventilation port 130 and the narrow sides face the side ventilation ports 120, airflow through the housing 100 may be enhanced. In one embodiment, an apparatus for generating airflow through the housing may be provided. The apparatus for generating airflow may be a fan, blower, or the like having moving parts, or may be an apparatus without moving parts such as an electrostatic fluid accelerator (EFA), or the like.

FIG. 4 is a schematic view of FIG. 3 taken in the direction of an arrow B, in which the rear ventilation port 130 of the housing 100 is omitted.

That is, since the fine dust sensor 300 is disposed on the path of air flowing between the first side ventilation 120a and the second side ventilation 120b provided in the housing 100, it is possible to easily measure the concentration of fine dusts contained in the air introduced into the housing 100.

When the air is introduced into the housing 100, the air may be introduced into the second side ventilation port 120b rather than the first side ventilation port 120a and may be discharged to the first side ventilation port 120a. However, for convenience of explanation, it will be described that the air is introduced into the first side ventilation port 120a and is discharged to the second side ventilation port 120b.

In addition, the housing 100 may have the first opening (105 in FIG. 2) and the second opening (107 in FIG. 2) at its top and bottom, respectively.

Specifically, the end face P1 of the first opening may be formed at an acute angle with the end face P2 of the second opening.

That is, the end face of the second opening formed at the bottom of the housing 100 may be parallel to the ground and the end face P1 of the first opening may be at an acute angle with the end face P2 of the second opening. This can be confirmed by the fact that a line L1 crossing the end face P1 of the first opening forms an acute angle A with a line L2 parallel to a line crossing the end face P2 of the second opening.

In this manner, when the end face P1 of the first opening forms an acute angle with the end face P2 of the second opening, the display unit (700 of FIG. 2) provided on the display plate (530 in FIG. 2) coupled to the first opening (105 in FIG. 2) may also be disposed at an acute angle with the ground. Accordingly, a user can visually and easily grasp the information on indoor temperature/humidity, fine dust concentration, $CO_2$ concentration and power consumption through the display unit (700 of FIG. 2) mounted on the display plate (530 of FIG. 2).

That is, if the display plate is disposed in parallel with the ground, the display unit mounted on the top of the display plate can also be disposed in parallel with the ground. In this case, it is difficult for the user to grasp the information displayed on the display unit at a long distance from the viewing angle of the display unit. However, as in the present disclosure, when the display plate (530 of FIG. 2) is disposed at an acute angle with the ground, the display unit (700 of FIG. 2) is also obliquely disposed so that, even when the user is at a remote distance, the sight line of the user and the display unit (700 in FIG. 2) can be opposed to face each other. Accordingly, the user can visually and easily grasp the information on indoor temperature/humidity, fine dust concentration, $CO_2$ concentration and power consumption through the display unit (700 of FIG. 2) mounted on the display plate (530 of FIG. 2).

Referring back to FIGS. 1 and 2, the support bracket 200 may be provided in the housing 100.

Specifically, the fine dust sensor 300 may be disposed at the rear bottom of the support bracket 200, the $CO_2$ sensor 350 may be disposed at the rear top of the support bracket 200, the temperature/humidity sensor 400 may be disposed in the front of the support bracket 200, and the main board 450 may be disposed on the top of the support bracket 200.

Here, the $CO_2$ sensor 350 may be disposed at the top of the fine dust sensor 300.

The correction sensor 410 may be disposed at the front bottom of the support bracket 200, that is, at the bottom of the temperature/humidity sensor 400, but is not limited thereto. In other words, the correction sensor 410 may be disposed at other portions such as a lateral surface and a rear surface of the support bracket 200.

In this manner, the support bracket 200 serves to fix and support the various components provided in the housing 100.

The fine dust sensor 300 provided in the housing 100 can sense the concentration of fine dusts introduced through the ventilation ports 120 and 130.

Specifically, as described above, the fine dust sensor 300 can sense the concentration of fine dusts contained in the air introduced through one of the first side ventilation port 120a and the second side ventilation port 120b and discharged through the other. Of course, the fine dust sensor 300 can also detect the concentration of fine dusts contained in the air introduced through the rear ventilation port 130.

That is, the fine dust sensor 300 can detect the concentration of fine dusts contained in the air introduced through not only the first side ventilation port 120a but also the second side ventilation port 120b.

However, due to the nature of fine dust concentration changing in real time, the concentration of fine dusts contained in the air flowing dynamically rather than the static air (that is, air having a low moving speed or flow rate) may be close to the actual concentration of fine dusts and therefore, it may be difficult to detect a change in fine dust concentration only with the fine dusts contained in the static air.

For this reason, the housing 100 is provided with the first side ventilation port 120a and the second side ventilation port 120b so that the fine dust sensor 300 can easily detect the concentration of fine dusts contained in the air introduced through the first side ventilation port 120a or the second side ventilation port 120b. Moreover, the first and second side ventilation ports 120a and 120b may be positioned across from each other to allow airflow through the housing.

Now, an example of fine dust concentration calculation logic of the fine dust sensor 300 will be described with reference to FIG. 5.

Referring to FIG. 5, in the fine dust sensor 300, assuming that a high level signal (High) is Vcc (supply voltage) and a low level signal (Low) is GND (ground state), the fine dust concentration can be calculated by dividing the sum of times (t1+t2+t3) corresponding to a section where the low level signal (Low) is generated by the total measurement time t (for example, 5 to 30 seconds) and then multiplying a result of the division by 100.

Of course, the fine dust concentration calculation logic may be varied depending on the type of fine dust sensor. However, for convenience of explanation, the present disclosure will be described by way of example in which the fine dust concentration is calculated through the calculation logic.

Referring again to FIGS. 1 and 2, the $CO_2$ sensor 350 disposed within the housing 100 can sense the concentration of $CO_2$ introduced through the ventilation ports 120 and 130.

Specifically, the $CO_2$ sensor 350 can sense the concentration of $CO_2$ contained in the air introduced through the first side ventilation port 120a, the second side ventilation port 120b and the rear ventilation port 130.

However, due to the nature of $CO_2$ concentration having a small variation range, there is no problem with the accuracy of measurement of the concentration of $CO_2$ contained in the static air (that is, air having a low moving speed or flow rate), unlike the measurement of the fine dust concentration.

For this reason, the $CO_2$ sensor 350 can measure the correct concentration of $CO_2$ contained not only in the air introduced through the first side ventilation port 120a and the second side ventilation port 120b but also in the air introduced through the rear ventilation port 130. The $CO_2$ sensor 350 may be positioned to face the rear ventilation port 130.

The temperature/humidity sensor 400 disposed in the housing 100 can sense temperature and humidity around the housing 100.

Specifically, the temperature/humidity sensor 400 disposed in the front of the support bracket 200 may be disposed adjacent to the front ventilation port 110 of the housing 100.

Accordingly, the temperature/humidity sensor 400 can more accurately measure the temperature/humidity around the housing, that is, the room temperature/humidity, through the front ventilation port 110.

The correction sensor 410 can sense the temperature/humidity inside the housing 100 and can correct the temperature/humidity around the housing 100 sensed by the temperature/humidity sensor 400.

Specifically, heat may be generated in each device or apparatus in the housing 100 and a measured value of the temperature/humidity sensor 400 may be inaccurate due to such heat. Accordingly, the correction sensor 410 can sense the temperature/humidity inside the housing 100 and correct the temperature/humidity around the housing 100 sensed by the temperature/humidity sensor 400, thereby providing more accurate temperature and humidity information to the user.

The main board 450 disposed in the housing 100 may include a processor 452 for controlling the plurality of light emitting units 610 and the display unit 700 based on data on the fine dust concentration and the $CO_2$ concentration provided respectively from the fine dust sensor 300 and the $CO_2$ sensor 350.

Referring to FIGS. 5 and 6, the main board 450 may include the processor 452 capable of RF (Radio Frequency) communication and controlling the plurality of light emitting units 610 and the display unit 700.

Specifically, the main board 450 may include the processor 452, a memory 454 and an RF communication unit 456.

The processor 452 capable of RF communication can control or communicate with the memory 454, the temperature/humidity sensor 400, the $CO_2$ sensor 350, the fine dust sensor 300, the display unit 700, the RF communication unit 456, the plurality of light emitting units 610 and the correction sensor 410.

For example, the processor 452 can communicate with the memory 454 through I2C (Inter Integrated Circuit), the fine dust sensor 300 through PWM (Pulse Width Modulation), the display unit 700 through SPI (Serial Peripheral Interface), the RF communication unit 456 through UART (Universal Asynchronous Receiver/Transmitter), the plurality of light emitting units 610 through GPO (General Purpose Output), and the correction sensor 410 ADC (Analog-Digital Converter).

Of course, this is just an example and communication between the processor 452 and each component is not limited thereto.

The processor 452 can also receive data on the concentration of fine dust and the concentration of $CO_2$ from the fine dust sensor 300 and the CO2 sensor 350, respectively, and control the plurality of light emitting units 610 and the display unit 700 based on the received data on the concentration of fine dust and the concentration of $CO_2$.

The processor 452 can also receive data on power consumption from an external wireless power meter through RF communication (RF) and control the plurality of light emitting units 610 and the display unit 700 based on the received data on power consumption.

The control method of the processor 452 will be described later.

The memory 454 can communicate with the processor 452 through I2C. The memory 454 may be, for example, an electrically erasable programmable read-only memory (EEPROM). When the processor 452 updates radio frequency firmware by wireless, the memory 454 can be used as a temporary data space.

Of course, the memory 454 can store data sensed by each sensor (the fine dust sensor 300, the temperature/humidity sensor 400, the $CO_2$ sensor 350 or the like) or store data on power consumption received from the external wireless power meter, but a detailed description thereof will be omitted.

The RF communication unit 456 can communicate with the processor 452 through UART. In addition, the RF communication unit 456 can wirelessly communicate with an external server 920 or a device though WiFi (Wireless Fidelity), for example.

Accordingly, the sensor hub 1 of the present disclosure can receive various information, such as time information and external weather information, from the external server 920. In addition, sensor hub 1 can wirelessly communicate with an external device, for example, a smart phone or the like to receive various information.

The sensor hub 1 of the present disclosure may further include a power supply unit 800 for supplying power to the components shown in FIG. 6.

Referring again to FIGS. 1 and 2, the display unit 700 provided on the top of the display plate 530 can display one of the temperature/humidity around the housing 100 (i.e., the indoor temperature and humidity), the fine dust concentration, the $CO_2$ concentration and the power consumption.

Specifically, the display unit 700 is mounted on the display plate 530 and can be controlled by the processor (452 in FIG. 6) provided in the main board 450.

Referring to FIGS. 8 and 9, the display unit 700 may include a first display unit 740 that displays information currently being checked, and a second display unit 750 that displays the main contents of the information.

The first display unit 740 may include a first icon 710 indicating a power consumption display mode, a second icon 720 indicating a $CO_2$ concentration display mode, and a third icon 730 indicating a fine dust concentration display mode.

The user can perform mode conversion in the right direction or the left direction by touching or pressing the first input unit 580. For every mode conversion, a conversion target icon (for example, the third icon 730) may be turned on and the previous icon (e.g., the second icon 720 or the first icon 710) may be turned off.

In addition, the second display unit 750 can display the main information corresponding to the display mode selected by the user.

Specifically, when the user selects the power consumption display mode to turn on the first icon 710, the second display unit 750 can display, for example, real-time power consumption, daily accumulated power consumption, or accumulated usage fee. When the user selects the $CO_2$ concentration display mode to turn on the second icon 720, the second display unit 750 can display, for example, a $CO_2$ value or $CO_2$ status information (for example, Good, Not Good and Bad). When the user selects the fine dust concentration display mode to turn on the third icon 730, the second display unit 750 can display, for example, a fine dust level or fine dust status information (for example, Good, Not Good and Bad).

Although not shown in the figures, when the user selects a home mode other than the first to third icons 710, 720 and 730 by touching or pressing the first input unit 580, the first to third icons 710, 720 and 730 are all turned off and the current time or the indoor temperature/humidity can be displayed on the second display unit 750. Moreover, in certain embodiments, the display unit 700 may display one or more types of information at the same time, such as indoor temperature/humidity, the $CO_2$ value or $CO_2$ status information, a fine dust level or fine dust status information, and/or power consumption information.

Referring again to FIGS. 1 and 2, the display plate 530 is coupled to the first opening 105 and the display unit 700 can be mounted on the display plate 530.

That is, the display plate 530 can serve to fix and support the display unit 700. As described above, the display plate 530 is coupled to the first opening 105 so that the display unit 700 provided on the display plate 530 can also be inclined to form an acute angle with the ground, thereby allowing the user to visually and easily grasp the information on indoor temperature/humidity, fine dust concentration, $CO_2$ concentration and power consumption.

The top plate 560 is disposed on the top of the display plate 530 and may be made of a transparent material.

Specifically, since the top plate 560 is made of a transparent material (for example, glass or acryl), the user can check the information displayed on the display unit 700 positioned at the bottom of the top plate 560.

The first input unit 580 is mounted on the top plate 560 and may receive an input from the user and provide it to the main board 450, that is, the processor (452 in FIG. 6).

Specifically, the user can change the display mode of the display unit 700 through the first input unit 580. That is, the user can perform the mode conversion in the right direction or the left direction by touching or pressing the first input unit 580. For every mode conversion, the conversion target icon is turned on and the previous icon is turned off.

In addition, the user can change an instant power screen as well as the general screen (display mode) described above through the first input unit 580 and can also use a buzzer function.

The illumination control board 480 is disposed at the bottom of the support bracket 200 and the top of the illumination plate 600 and can turn on or off the plurality of light emitting units 610 based on a control signal received from the processor 452.

However, in the present disclosure, the illumination control board 480 may be omitted, in which case the plurality of light emitting units 610 may be turned on or off based on the control signal received directly from the processor 452.

The second input unit 590 may be provided on the rear surface of the housing 100.

Specifically, the second input unit 590 may be disposed on the rear surface of the housing 100, that is, between the vents of the rear ventilation port 130.

Further, the user can turn on/off the display unit 700 or switch between a setting mode and an operation mode by touching or pressing the second input unit 590, for example.

Although not shown in the figures, a third input unit (not shown) may be mounted on the bottom plate 630 and the user may perform factory initialization, reset, etc. by touching or pressing the third input unit, for example.

The illumination plate 600 is coupled to the second opening 107 and the plurality of light emitting units 610 may be mounted on the illumination plate 600.

Specifically, the illumination plate 600 can serve to fix and support the plurality of light emitting units 610. Further, the illumination plate 600 may be disposed parallel to the ground by being coupled to the second opening 107, as described above.

Since the edge portion 605 of the illumination plate 600 is made of a translucent material or a transparent material, the user can check light emitted from the plurality of light-emitting units 610 through the edge portion 605 of the illumination plate 600.

That is, the user can visually and easily grasp the information on fine dust concentration, $CO_2$ concentration and power consumption even at a remote distance by checking the light emitted from the plurality of light emitting units 610 through the edge portion 605 of the illumination plate 600.

In some embodiment, the plurality of light emitting units 610 may be disposed apart at regular intervals along the edge portion 605 of the illumination plate 600, and may be controlled by the processor (452 in FIG. 6). Each of the plurality of light emitting units 610 may be, for example, an LED, but is not limited thereto.

The color of the light emitted from the plurality of light emitting units 610 may vary depending on one of the fine dust concentration, the $CO_2$ concentration and the power consumption and such variation in color can be controlled by the processor (452 in FIG. 6).

The bottom plate 630 is provided with an anti-slip member 650 at a lower portion thereof and may be disposed at the bottom of the illumination plate 600.

Specifically, the bottom plate 630 serves to protect the plurality of light emitting units 610 mounted on the illumination plate 600 from an external impact or the like by being disposed at the bottom of the illumination plate 600.

The anti-slip member 650 provided at the lower portion of the bottom plate 630 may be formed in plural (650a and 650b) and may be made of a rubber material. The sliding of the sensor hub 1 can be prevented by the anti-slip member 650.

As described above, the sensor hub 1 according to an embodiment of the present disclosure senses the indoor temperature/humidity, the fine dust concentration and the $CO_2$ concentration through the temperature/humidity sensor 400, the fine dust sensor 300 and the $CO_2$ sensor 350, respectively, so that the user can be provided with information useful in daily life. Particularly, the sensor hub 1 senses and displays the fine dust concentration and the $CO_2$ concentration in real time, so that the user can naturally recognize the point of time of using an air cleaner and the point of time required for ventilation through the opening and closing of a window even with little or no user interaction, thereby making it possible to improve user convenience.

In addition, the sensor hub 1 according to an embodiment of the present disclosure is configured such that the external air is introduced into the housing 100 through the rear ventilation port 130 and the first and second side ventilation ports 120 provided in the housing 100 so that the fine dust concentration and the $CO_2$ concentration can be easily detected. Furthermore, by reducing the probability that the fine dust concentration and the $CO_2$ concentration are erroneously measured, it is possible to provide more accurate and reliable information to the user.

In addition, the sensor hub 1 according to an embodiment of the present disclosure can display the information on one or more of indoor temperature/humidity, fine dust concentration, $CO_2$ concentration and/or power consumption through display unit 700 provided in the display plate 530 forming an acute angle with the ground so that the user can easily check the information even if the user does not move to the vicinity of the sensor hub 1 even at a remote distance. In addition, the user can check the light emitted from the plurality of light emitting units 610 through the edge portion 605 of the illumination plate 600, thereby enabling the user to visually and easily grasp the schematic information on fine dust concentration, $CO_2$ concentration and power consumption even at a remote distance, which can result in improved user convenience and satisfaction.

Hereinafter, a control flow of the sensor hub of FIG. 1, that is, a method of operating the sensor hub will be described with reference to FIG. 10.

Figure 10:
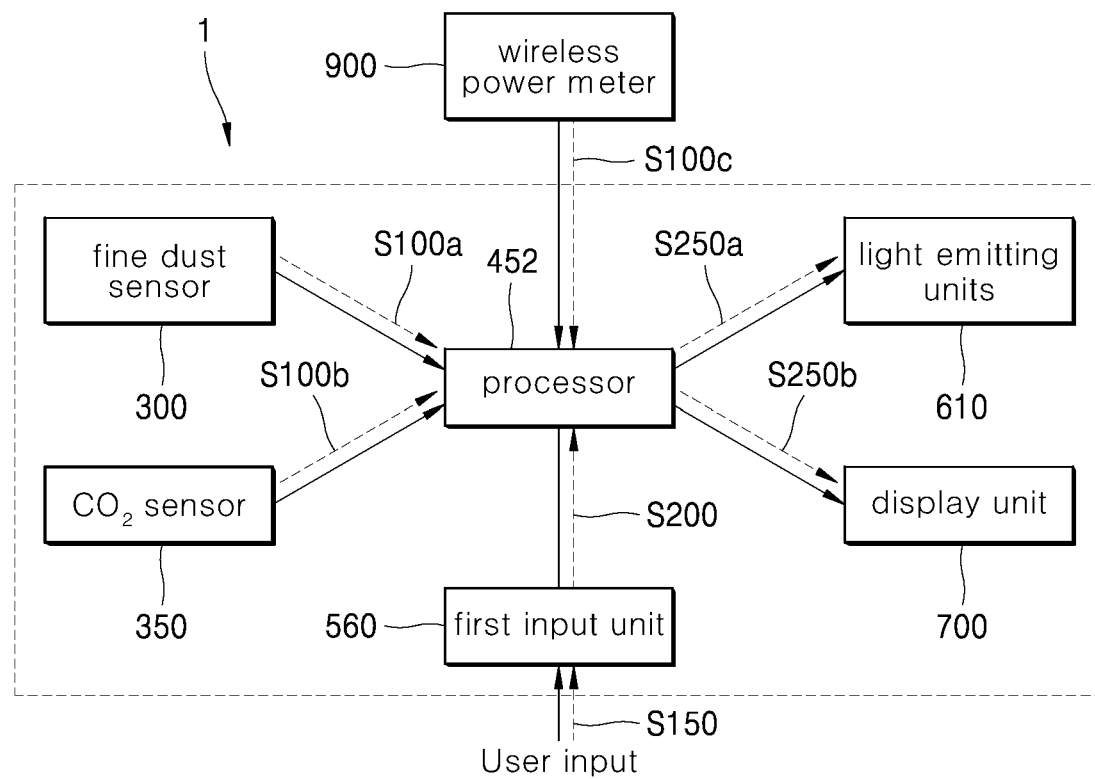
FIG. 10 is a block diagram for explaining a control flow of the sensor hub of FIG. 1.

FIG. 10 is a block diagram illustrating the control flow of the sensor hub of FIG. 1. in FIG. 10, for convenience of explanation, some of the components of the above-described sensor hub are omitted.

Referring to FIG. 10, first, the concentration of fine dusts introduced into the housing 100 is sensed using the fine dust sensor 300 (S00a).

Specifically, the fine dust sensor 300 can sense the concentration of fine dusts introduced into the housing 100 through the above-described process and provide the processor 452 with data on the sensed fine dust concentration.

The concentration of $CO_2$ introduced into the housing 100 is sensed using the $CO_2$ sensor 350 (S100b).

Specifically, the CO2 sensor 350 can sense the concentration of $CO_2$ introduced into the housing 100 through the above-described process and provide the processor 452 with data on the sensed $CO_2$ concentration.

The processor 452 capable of RF communication receives data on power consumption from the external wireless power meter 900 (S100c).

Specifically, the processor 452 capable of RF communication the data on power consumption from the external wireless power meter 900 in real time.

The data provided from the fine dust sensor 300, the $CO_2$ sensor 350 and the wireless power meter 900 may be directly provided to the processor 452 but may be stored in the memory (454 in FIG. 6).

The steps S100a, S100b and S100c may be performed at the same time or may be changed in the proceeding order.

An input is received from the user (S150).

Specifically, the user can select a mode for information (for example, power consumption, time, indoor temperature/humidity, fine dust concentration, $CO_2$ concentration, etc.) to be checked by touching or pressing the first input unit 580.

The input received from the user is provided to the processor 452 (S200).

Specifically, the first input unit 580 can provide the input received from the user to the processor 452.

The plurality of light emitting units and the display unit are controlled based on data on any one of the fine dust concentration, the $CO_2$ concentration and the power consumption (S250a and S250b).

Specifically, the processor 452 can compare the data on any one of the fine dust concentration, the $CO_2$ concentration and the power consumption with a predetermined reference value based on the input received from the user, that is, the input of the user provided from the first input unit 580, and control the plurality of light emitting units 610 and the display unit 700 based on a result of the comparison.

Here, the predetermined reference value may be any one of a predetermined reference value for the fine dust concentration, a predetermined reference value for the $CO_2$ concentration, and a predetermined reference value for the power consumption.

That is, for example, if the input received from the user is an input indicative of a mode for the fine dust concentration, the processor 452 can compare the data on the fine dust concentration with the predetermined reference value for the fine dust concentration.

The processor 452 can control the plurality of light emitting units 610 and the display unit 700 based on the comparison result.

Specifically, when the value of the data for any one of the fine dust concentration, the $CO_2$ concentration and the power consumption is larger than the predetermined reference value, the processor 452 can control the plurality of light emitting units 610 to emit light of a first color (for example, red).

On the other hand, when the value of the data for any one of the fine dust concentration, the $CO_2$ concentration and the power consumption is smaller than the predetermined reference value, the processor 452 can control the plurality of light emitting units 610 to emit light of a second color (for example, blue) different from the first color.

In addition, when the value of the data for any one of the fine dust concentration, the $CO_2$ concentration and the power consumption is larger than the predetermined reference value, the processor 452 can control the display unit 700 to display first information (for example, Bad).

On the other hand, when the value of the data for any one of the fine dust concentration, the $CO_2$ concentration and the power consumption is smaller than the predetermined reference value, the processor 452 can control the display unit 700 to display second information (for example, Good) different from the first information.

When there is a plurality of predetermined reference values for the fine dust concentration, the processor 452 may compare the data on the fine dust concentration with each of the reference values.

For example, when the predetermined reference value for the fine dust concentration includes a first reference value and a second reference value smaller than the first reference value, the processor 452 can compare the predetermined reference value for the fine dust concentration with both of the first reference value and the second reference value. When the corresponding data value is equal to or greater than the first reference value, the processor 452 can make determination for a case where the data value is between the first reference value and the second reference value and a case where the data value is equal to or smaller than the second reference value.

Further, when the corresponding data value is equal to or greater than the first reference value, the processor 452 can control the plurality of light emitting units 610 to emit the light of the first color (for example, red) and the display unit 700 to display the first information (for example, Bad).

When the corresponding data value is between the first reference value and the second reference value, The processor 452 can control the plurality of light emitting units 610 to emit light of a third color (for example, yellow) and the display unit 700 to display third information (for example, Not Good).

When the corresponding data value is equal to or smaller than the second reference value, the processor 452 can control the plurality of light emitting units 610 to emit the light of the second color (for example, blue) and the display unit 700 to display the second information (for example, Good).

Upon receiving the user input from the first input unit 580, the processor 452 can directly compare data corresponding to the user input among the data received from the fine dust sensor 300, the $CO_2$ sensor 350 and the wireless power meter 900 with a predetermined reference value. Of course, upon receiving the user input from the first input unit 580, the processor 452 can read data corresponding to the user input among the data stored in the memory 454 and compare the read data with the predetermined reference value.

Although not shown in the figures, if the user selects the above-described home mode (i.e., the mode for the current time or the indoor temperature/humidity rather than the fine dust concentration, the $CO_2$ concentration and the power consumption), the processor 452 can control the display unit 700 to display the indoor temperature/humidity or the current time without performing the above-described comparing process. Of course, in this case, the processor 452 can control the plurality of light emitting units 610 to remain at the turn-off state.

As described above, the method of operating the sensor hub 1 according to the present disclosure includes a step of comparing data on any one of the fine dust concentration, the $CO_2$ concentration and the power consumption with a predetermined reference value based on the input received from the user, and a step of controlling the plurality of light emitting units 610 and the display unit 700 based on a result of the comparison. That is, the user can directly select the information to be checked and intuitively grasp the contents of the information through the plurality of light emitting units 610 or the display unit 700.

It is an object of the present disclosure to provide a sensor hub capable of providing information useful for users in real life by sensing fine dust concentration, $CO_2$ concentration and room temperature and humidity (hereinafter referred to as temperature/humidity) by using built-in sensors.

It is another object of the present disclosure to provide a sensor hub having an external structure capable of easily detecting fine dust concentration and $CO_2$ concentration.

It is another object of the present disclosure to provide a sensor hub that allows users to visually and easily grasp information on indoor temperature/humidity, fine dust concentration, $CO_2$ concentration and power consumption.

It is another object of the present disclosure to provide a method for operating a sensor hub for displaying information on fine dust concentration, $CO_2$ concentration and power consumption so that the users can intuitively grasp the information.

Objects of the present disclosure are not limited to the above-described objects and other objects and advantages can be appreciated by those skilled in the art from the following descriptions. Further, it will be easily appreciated that the objects and advantages of the present disclosure can be practiced by means recited in the appended claims and a combination thereof.

A sensor hub according to the present disclosure includes a temperature/humidity sensor, a fine dust sensor and a $CO_2$ sensor for detecting indoor temperature/humidity, fine dust concentration and $CO_2$ concentration, respectively, thereby providing users with useful information in real life.

According to one aspect of the present disclosure, there is provided a sensor hub including: a housing having ventilation ports on its lateral and rear sides, respectively, and having a first opening and a second opening at its top and bottom, respectively; a fine dust sensor provided in the housing for sensing the concentration of fine dusts introduced through the ventilation ports; a $CO_2$ sensor provided in the housing for sensing the concentration of $CO_2$ introduced through the ventilation ports; a display plate coupled to the first opening and having a display unit mounted thereon; an illumination plate coupled to the second opening and having a plurality of light emitting units mounted thereon; and a main board disposed in the housing and including a processor for controlling the plurality of light emitting units and the display unit based on data on the fine dust concentration and the $CO_2$ concentration received respectively from the fine dust sensor and the $CO_2$ sensor.

According to another aspect of the present disclosure, there is provided a sensor hub including: a housing having ventilation ports on its lateral and rear sides, respectively, and having a first opening and a second opening at its top and bottom, respectively; a fine dust sensor provided in the housing for sensing the concentration of fine dusts introduced through the ventilation ports; a display plate coupled to the first opening and having a display unit mounted thereon; an illumination plate coupled to the second opening and having a plurality of light emitting units mounted thereon; and a main board disposed in the housing and including a processor for controlling the plurality of light emitting units and the display unit based on data on the fine dust concentration received from the fine dust sensor.

According to another aspect of the present disclosure, there is provided a method for operating a sensor hub, including: sensing the concentration of fine dusts introduced into a housing using a fine dust sensor and providing data on the sensed fine dust concentration to a processor; sensing the concentration of $CO_2$ introduced into the housing using a $CO_2$ sensor and providing data on the sensed $CO_2$ concentration to the processor; receiving data on power consumption from an external wireless power meter through the processor capable of RF communication; and controlling a plurality of light emitting units and a display unit based on data on any one of the fine dust concentration, the $CO_2$ concentration and the power consumption.

[Advantages of the Present Disclosure]

According to an embodiment of the present disclosure, the sensor hub can sense the indoor temperature/humidity, the fine dust concentration and the $CO_2$ concentration through the temperature/humidity sensor, the fine dust sensor and the $CO_2$ sensor, respectively, so that the user can be provided with information useful in daily life. Particularly, the sensor hub can sense and display the fine dust concentration and the $CO_2$ concentration in real time, so that the user can naturally recognize the point of time of using an air cleaner and the point of time required for ventilation through the opening and closing of a window even with little or no user interaction, thereby making it possible to improve user convenience.

According to an embodiment of the present disclosure, the sensor hub is configured such that the external air is introduced into the housing through the rear ventilation port and the first and second side ventilation ports provided in the housing so that the fine dust concentration and the $CO_2$ concentration can be easily detected. Furthermore, by reducing the probability that the fine dust concentration and the $CO_2$ concentration are erroneously measured, it is possible to provide more accurate and reliable information to the user.

According to an embodiment of the present disclosure, the sensor hub can display the information on indoor temperature/humidity, fine dust concentration, $CO_2$ concentration and power consumption through display unit provided in the display plate forming an acute angle with the ground so that the user can easily check the information even if the user does not move to the vicinity of the sensor hub even at a remote distance. In addition, the user can check the light emitted from the plurality of light emitting units through the edge portion of the illumination plate, thereby enabling the user to visually and easily grasp the schematic information on fine dust concentration, $CO_2$ concentration and power consumption even at a remote distance, which can result in improved user convenience and satisfaction.

According to an embodiment of the present disclosure, the method of operating the sensor hub includes a step of comparing data on any one of the fine dust concentration, the $CO_2$ concentration and the power consumption with a predetermined reference value based on the input received from the user, and a step of controlling the plurality of light emitting units and the display unit based on a result of the comparison. That is, the user can directly select the information to be checked and intuitively grasp the contents of the information through the plurality of light emitting units or the display unit.

The above and other effects of the present disclosure will be described below together with specific matters for carrying out the present disclosure.

It will be understood that when an element or layer is referred to as being "on" another element or layer, the element or layer can be directly on another element or layer or intervening elements or layers. In contrast, when an element is referred to as being "directly on" another element or layer, there are no intervening elements or layers present. As used herein, the term "and/or" includes any and all combinations of one or more of the associated listed items.

It will be understood that, although the terms first, second, third, etc., may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section could be termed a second element, component, region, layer or section without departing from the teachings of the present invention.

Spatially relative terms, such as "lower", "upper" and the like, may be used herein for ease of description to describe the relationship of one element or feature to another element (s) or feature(s) as illustrated in the figures. It will be understood that the spatially relative terms are intended to encompass different orientations of the device in use or operation, in addition to the orientation depicted in the figures. For example, if the device in the figures is turned over, elements described as "lower" relative to other elements or features would then be oriented "upper" relative the other elements or features. Thus, the exemplary term "lower" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Embodiments of the disclosure are described herein with reference to cross-section illustrations that are schematic illustrations of idealized embodiments (and intermediate structures) of the disclosure. As such, variations from the shapes of the illustrations as a result, for example, of manufacturing techniques and/or tolerances, are to be expected. Thus, embodiments of the disclosure should not be construed as limited to the particular shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Any reference in this specification to "one embodiment," "an embodiment," "example embodiment," etc., means that a particular feature, structure, or characteristic described in connection with the embodiment is included in at least one embodiment. The appearances of such phrases in various places in the specification are not necessarily all referring to the same embodiment. Further, when a particular feature, structure, or characteristic is described in connection with any embodiment, it is submitted that it is within the purview of one skilled in the art to effect such feature, structure, or characteristic in connection with other ones of the embodiments.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. A sensor hub comprising:
   a housing having ventilation ports on a front side, lateral sides and a rear side of the housing, and the housing having a first opening and a second opening at a top end and a bottom end of the housing, respectively;
   a fine dust sensor disposed adjacent to at least one of the ventilation ports of the housing and configured to sense a concentration of fine dust introduced through the ventilation ports;
   a $CO_2$ sensor disposed adjacent to the ventilation ports of the housing and configured to sense a concentration of $CO_2$ introduced through the ventilation ports;
   a temperature/humidity sensor disposed adjacent to at least one of the ventilation ports of the housing for sensing temperature and humidity around the housing;
   a correction sensor disposed adjacent to the temperature/humidity sensor for sensing temperature and humidity inside the housing, and the correction sensor for correcting the sensed temperature and the humidity around the housing based on the sensed temperature and the humidity inside the housing;
   a display plate coupled to the first opening and a display unit mounted to the display plate;
   an illumination plate coupled to the second opening and having an edge portion made of a transparent or translucent material;
   a plurality of light emitting units disposed apart from each other along the edge portion of the illumination plate for emitting light of a same color; and
   a main board disposed in the housing and including a processor configured to control the plurality of light emitting units and the display unit based on data regarding the fine dust concentration, the $CO_2$ concentration and the corrected temperature and humidity,
   wherein the light emitted by the plurality of light emitting units passes through the edge portion of the illumination plate,
   the processor is configured to:
      control the color of the light emitted from the plurality of light emitting units by comparing the data regarding one or more of the fine dust concentration and the $CO_2$ concentration with a predefined reference value, and
      control the display unit to display information regarding the fine dust concentration, the $CO_2$ concentration or the corrected temperature and humidity.

2. The sensor hub of claim 1, wherein the ventilation ports include a front ventilation port provided on a front side of the housing,
   wherein the temperature/humidity sensor is disposed adjacent to the front ventilation port.

3. The sensor hub of claim 1, wherein the processor receives data on power consumption from an external wireless power meter through radio frequency communication and controls the plurality of light emitting units and the display unit based on the received power consumption data.

4. The sensor hub of claim 1, further comprising a support bracket provided in the housing.

5. The sensor hub of claim 4, wherein the fine dust sensor is disposed on a rear bottom portion of the support bracket,
   wherein the $CO_2$ sensor is disposed over a top of the fine dust sensor,
   wherein the temperature/humidity sensor is disposed on a front portion of the support bracket, and
   wherein the main board is disposed on an upper surface of the support bracket.

6. The sensor hub of claim 1, further comprising:
   a top plate disposed over the display plate and made of a transparent material; and
   a bottom plate provided with an anti-slip member at a lower portion and disposed under the illumination plate.

7. The sensor hub of claim 1, wherein the first opening at the top end of the housing is formed at a first angle relative to the lateral sides and the rear side of the housing, and the second opening at the bottom end of the housing is formed at a second angle relative to the lateral sides and the rear side of the housing, wherein the first angle of the first opening forms an acute angle relative to the second angle of the second opening.

8. The sensor hub of claim 1, wherein the ventilation ports include:
   a rear ventilation port provided on the rear side of the housing; and
   first and second side ventilation ports provided on the lateral sides of the housing.

9. The sensor hub of claim 8, wherein air introduced through one of the first and second side ventilation ports is discharged through the other one of the first and second side ventilation ports.

10. The sensor hub of claim 8, wherein the first side ventilation port and the second side ventilation port are provided on opposite lateral sides of the housing.

11. The sensor hub of claim 10, wherein the fine dust sensor is positioned in the housing between the first side ventilation port and the second side ventilation port.

12. A method for operating a sensor hub, comprising:
   sensing, by a fine dust sensor, a concentration of fine dust introduced into a housing and providing, to a processor, data on the sensed fine dust concentration;
   sensing, by a $CO_2$ sensor, a concentration of $CO_2$ introduced into the housing and providing, to the processor, data on the sensed $CO_2$ concentration;
   sensing, by a temperature/humidity sensor, temperature and humidity around the housing;
   sensing, by a correction sensor, temperature and humidity inside the housing;

correcting, by the correction sensor, the sensed temperature and the humidity around the housing based on the sensed temperature and the humidity inside the housing;

receiving data, at a processor, regarding power consumption from an external wireless power meter through the processor which is configured for RF communication; and controlling a plurality of light emitting units and a display unit based on data regarding one or more of the fine dust concentration, the $CO_2$ concentration, the power consumption and the corrected temperature and humidity, wherein the controlling of the plurality of light emitting units and the display unit includes:
comparing the data regarding one or more of the fine dust concentration, the $CO_2$ concentration and the power consumption with a predetermined reference value,
controlling a color of light emitted from the plurality of light emitting units unit based on a result of the comparing, wherein the plurality of light emitting units emit light of a same color, and
controlling the display unit to display information regarding the fine dust concentration, the $CO_2$ concentration, the power consumption or the corrected temperature and the humidity.

13. The method of claim 12, wherein the predetermined reference value is one of a predetermined reference value for the fine dust concentration, a predetermined reference value for the $CO_2$ concentration, and a predetermined reference value for the power consumption.

14. The method of claim 12, wherein the processor controls the plurality of light emitting units to emit light of a first color when a value of data regarding any one of the fine dust concentration, the $CO_2$ concentration and the power consumption is greater than the predetermined reference value, and wherein the processor controls the plurality of light emitting units to emit light of a second color different than the first color when the value of data regarding any one of the fine dust concentration, the $CO_2$ concentration and the power consumption is less than the predetermined reference value.

15. The method of claim 12, wherein the processor controls the display unit to display first information when a value of data regarding any one of the fine dust concentration, the $CO_2$ concentration and the power consumption is greater than the predetermined reference value, and wherein the processor controls the display unit to display second information different from the first information when the value of data regarding any one of the fine dust concentration, the $CO_2$ concentration and the power consumption is less than the predetermined reference value.

* * * * *